United States Patent
Eckert et al.

(10) Patent No.: US 9,482,601 B2
(45) Date of Patent: Nov. 1, 2016

(54) PORTABLE DEVICE FOR TRANSPORTING A HISTOLOGICAL SAMPLE

(71) Applicant: Leica Biosystems Nussloch GmbH, Nussloch (DE)

(72) Inventors: Ralf Eckert, Schriesheim (DE); Michael Eberhard, Rheingönheim (DE)

(73) Assignee: LEICA BIOSYSTEMS NUSSLOCH GMBH, Nussloch (DE)

( * ) Notice: Subject to any disclaimer, the term of this patent is extended or adjusted under 35 U.S.C. 154(b) by 101 days.

(21) Appl. No.: 14/061,339

(22) Filed: Oct. 23, 2013

(65) Prior Publication Data

US 2014/0120011 A1 May 1, 2014

(30) Foreign Application Priority Data

Oct. 26, 2012 (DE) .................. 10 2012 219 684

(51) Int. Cl.
| | |
|---|---|
| *A61B 10/00* | (2006.01) |
| *G01N 1/31* | (2006.01) |
| *B01L 7/00* | (2006.01) |
| *G01N 1/42* | (2006.01) |
| *G01N 1/06* | (2006.01) |
| *G01N 1/36* | (2006.01) |

(52) U.S. Cl.
CPC . *G01N 1/31* (2013.01); *B01L 7/00* (2013.01); *G01N 1/42* (2013.01); *B01L 2300/1822* (2013.01); *B01L 2300/1894* (2013.01); *G01N 1/06* (2013.01); *G01N 1/36* (2013.01)

(58) Field of Classification Search
CPC .................................. B01L 9/52; B01L 7/00
See application file for complete search history.

(56) References Cited

U.S. PATENT DOCUMENTS

| | | | |
|---|---|---|---|
| 2005/0226770 A1* | 10/2005 | Allen | .................. G01N 1/36 422/63 |
| 2006/0005562 A1 | 1/2006 | Heid et al. | |
| 2007/0196237 A1 | 8/2007 | Neuzil et al. | |
| 2007/0204734 A1 | 9/2007 | Ito et al. | |
| 2008/0041069 A1 | 2/2008 | Vicar et al. | |

(Continued)

FOREIGN PATENT DOCUMENTS

| | | |
|---|---|---|
| DE | 10244055 A1 | 4/2004 |
| DE | 10 2010 010 694 A1 | 9/2011 |

(Continued)

OTHER PUBLICATIONS

Leica Mikrosysteme GmbH, Leica EM VCT100: Vacuum Cryo Transfer from Preparation to Analysis, available online at least as of May 2014.

*Primary Examiner* — Jyoti Nagpaul
(74) *Attorney, Agent, or Firm* — Hodgson Russ LLP

(57) ABSTRACT

The invention relates, in accordance with one aspect, to a portable device for transporting at least one histological sample or at least one cassette containing a histological sample. The device is attachable to a processing station for processing 5 histological samples. In the attached state, energy for cooling the histological sample is transferred from the processing station to the device or vice versa. In accordance with another aspect of the invention, a processing station for processing a histological sample is provided, which station is embodied for releasable attachment of a portable device. The processing station is further embodied to transfer energy 10 for cooling to, or receive it from, an attached device.

22 Claims, 2 Drawing Sheets

(56) References Cited

U.S. PATENT DOCUMENTS

2010/0086964 A1* 4/2010 Walter et al. .............. 435/40.52
2011/0239792 A1 10/2011 Sato et al.

FOREIGN PATENT DOCUMENTS

| GB | 2479968 A | 2/2011 |
| WO | 2008074073 A1 | 6/2008 |

* cited by examiner

PORTABLE DEVICE FOR TRANSPORTING A HISTOLOGICAL SAMPLE

CROSS REFERENCE TO RELATED APPLICATIONS

This application claims priority of German patent application number 10 10 2012 219 684.6 filed Oct. 26, 2012, the entire disclosure of which is incorporated by reference herein.

FIELD OF THE INVENTION

The invention relates to a portable device for transporting at least one histological sample or at least one cassette containing a histological sample.

The invention further relates to a processing station for processing a histological sample.

BACKGROUND OF THE INVENTION

The purpose of processing with (usually) several processing stations is to bring a sample, taken from a patient, into a state that permits sectioning into thin layers with a microtome. Sectionability can be made possible, for example, by the fact that a medium that mechanically stabilizes the tissue is introduced (infiltrated) into the tissue in multiple successive processing steps. Alternatively, the tissue can also be frozen.

A plurality of processing stations for processing histological samples are already known from the existing art. Processing stations are known, for example, in the form of trimming stations, fixing stations, dehydration stations, cleaning stations, infiltration stations, embedding stations, or microtomes (sectioning stations), in a wide variety of embodiments.

In a trimming station, the tissue (for example, removed from a patient) is cut into individual samples. The samples are usually placed into cassettes and transported to a fixing station. Fixing of the samples is necessary because oxygen supply to the cells is interrupted after removal of the tissue from the patient, and this results in cell death. Cell death causes morphological changes that are referred to as "necrosis." Firstly a swelling of the cells can be observed, and protein denaturing and autolysis also occur. To counteract this damage, fixing of the removed samples with a fixing agent, for example formalin, occurs in the fixing station.

After treatment in the fixing station, dehydration of the samples occurs in a dehydration station. Dehydration of the samples is necessary in order to make possible the subsequent process of infiltration and embedding.

Because the fixing agent, in particular formalin, is usually an aqueous medium, whereas the infiltration or embedding agent (in particular paraffin) that is to be used is in most cases a medium not miscible with water, dehydration of the samples must be accomplished before further processing of the samples in an infiltration station. Dehydration of the samples is performed with the aid of dehydrating agent, such as e.g. ethanol.

Prior to transfer of the samples to the infiltration station, they are also cleaned. Cleaning is necessary because water and/or alcohol contaminants in the embedding agent, in particular paraffin, result in poor cutting characteristics with a microtome and therefore need to be avoided. Saline, xylene, etc. can be used, for example, as cleaning agents.

After processing of the sample in the cleaning station, it is brought to an infiltration station. In the infiltration station an infiltration agent, which usually corresponds to the embedding agent used later, is introduced into cavities of the sample until it is saturated. Introduction of the infiltration agent allows the samples to be mechanically stabilized.

Following processing of the sample in the infiltration station, it is processed in the embedding station. In the embedding station the histological sample is embedded into an embedding agent such as paraffin or wax. In practice, the term "embedding" is used in two ways. On the one hand it is a synonym for "infiltration," which occurs in the aforementioned infiltration station; on the other hand, it refers to the "embedding" or "block embedding" that occurs in the embedding station.

For embedding, the samples are placed into molds and the mold is filled with the embedding agent. The histological sample is then cooled so that the embedding agent can harden. To cool the histological samples they are, for example, placed onto a cooling plate of the embedding station. The result is to create an embedded block in which the sample is immobilized in stationary fashion. After hardening of the embedding agent, the sample can be sectioned with the microtome into individual thin sample sections, which in a subsequent step can be stained and investigated with a microscope.

To ensure that the sectioning operation with the microtome can be carried out precisely, it is necessary for the embedded block to remain in a hard state. In practice, a laboratory worker transports the cassettes individually from the embedding station to the microtome. Alternatively, it is known that the laboratory worker does not transport the cassettes individually, but instead places them from the cooling plate of the embedding station into a transport basket located next to the processing station. The transport basket is then transported to a microtome, with which the samples present in the transport basket can be processed.

With processing stations known from the existing art, the risk exists that, especially in warm regions, the embedded block may soften before the sample is processed using the microtome. Softening of the embedded block can occur when the samples are taken off the cooling plate and, for example, placed into the transport basket, and the latter is transported to the microtome only after a certain time has elapsed. A result of softening of the embedded block is that the sectioning operation with the microtome is difficult or in fact impossible.

A further disadvantage is the fact that transporting the cassettes individually between the embedding statin and the microtome is cumbersome and time-consuming. The use of transport baskets in turn has the disadvantage that additional components are used, which require additional storage space.

SUMMARY OF THE INVENTION

An object of the present invention is therefore to make available a portable device by means of which the process of treating the histological sample can be improved, and at the same time the disadvantages recited above can be avoided.

This object is achieved by a portable device of the kind recited previously which is characterized in that the device is attachable to a processing station for processing histological samples, where the device is embodied to cool the sample to be carried, and where, in the attached state, energy for cooling is transferrable from the processing station to the device or vice versa.

The portable device can serve to transport the histological samples, or the cassettes containing the sample, from one processing station to another processing station.

A portable device of this kind has the advantage that even during the transport of one or more samples from one processing station to the next processing station, cooling of the samples can occur continuously. This advantageously prevents the samples from heating up during transport. In addition, the portable device offers the advantage that a processed sample which is ready for transport, or a cassette filled with a sample, can be placed directly onto the portable device.

A portable device of this kind, preferably of modular embodiment, has the advantage that it enables an improved process of treating the histological sample. An improvement in the treatment process is possible because one working step in the context of transporting the samples from a first processing station to a second processing station is eliminated, as explained below.

In contrast to the embodiments known from the existing art, it is no longer necessary to transport the samples, in a separate working step, individually from a first processing station to a second processing station, or firstly to introduce them from the cooling plate of a first processing station into the transport basket and then transport them to a second processing station.

The working step is eliminated because, for example after hardening of the embedded block, the samples do not need to be individually transported or introduced into a transport basket, but instead the device carrying the samples can be moved from the first processing station to the second processing station, advantageously without interrupting the cooling of the samples.

Because the aforementioned working step is eliminated, the risk that an embedded block will soften prior to a sectioning operation is likewise reduced. This results because cooling of the sample occurs at each processing station, for example the embedding station and the microtome.

The portable device can be designed to receive at least two, in particular twenty, samples or cassettes.

The process of treating the histological sample can moreover be improved by the fact that the sample removed from the trimming station is placed onto the portable device, by means of which the sample is cooled. What is thereby possible is that the sample does not need to be introduced into the fixing agent immediately after trimming in order to avoid damage to the sample. Instead, the sample breakdown process is slowed because of the cooling, the result being to ensure that the further treatment process can be accomplished using a high-quality sample.

A further advantage of the embodiment recited above of the portable device is that a separate transport basket is no longer needed for the transport operation between two processing stations. This offers the advantage that a separate storage space for it is not required. Especially when the portable device is positionable in positively engaged fashion into a receptacle of a processing station, the receptacle of the processing station can instead serve as a storage space even when the processing station is not currently being used.

The portable device can comprise an active cooling device and/or a passive cooling device. The portable device can moreover comprise a reservoir for electrical energy. The active cooling device can be a Peltier element. The passing cooling device can be a cold reservoir such as a cold accumulator or a cold pack, or a (preferably liquid) coolant provided in the portable device. The provision of a cooling device in the portable device offers the advantage that cooling of the histological sample is possible even after the portable device has been detached from the processing station. It is thereby possible to ensure that the embedded block or the sample is also cooled during transport between two processing stations.

The energy necessary for cooling the histological sample can be transferred in the form of electrical energy and/or in the form of a heat flux and/or by conveying a coolant. The processing station can transfer electrical energy to the portable device. Alternatively or additionally, the processing station can receive a heat flux directed from the portable device to the processing station.

With the portable device in the state attached to the processing station, in addition to the histological sample, the cold accumulator and/or the coolant provided in the portable device can be cooled. Alternatively or additionally, with the portable device in the state attached to the processing station, energy, in particular electrical energy, can be delivered to the Peltier element and/or to the reservoir. In the context of energy delivery to the Peltier element, the latter can, in addition or alternatively to cooling by the processing station, cool the sample held by the portable device when the portable device is attached to the processing station.

After detachment of the portable device from the processing station, the active and/or passive cooling device, in particular the cold accumulator and/or Peltier element, can cool the histological sample or cassette. The Peltier element can obtain the electrical energy necessary for cooling from the reservoir arranged in the portable device.

In a particular embodiment of the portable device, at least one recess can be provided for reception of the sample or cassette. Provision of the recess offers the advantage that the sample or cassette is immobilized in stationary fashion in the portable device, and cooling of the sample or cassette is improved.

A further object of the present invention is to provide a processing station for processing a histological sample that improves the process of treating the histological sample.

The object is achieved by a processing station which is characterized in that the processing station is embodied for releasable attachment of a portable device, in particular a device described above, for transporting at least one histological sample or at least one cassette containing a histological sample, and is embodied to transfer energy for cooling to, or receive it from, an attached device.

A processing station of this kind has the advantage that an improvement in the process of treating the histological sample is achieved because of the cooling of the sample. As a result of the cooling of the sample it is possible to ensure, for example, that the embedded block does not soften after block embedding, for example in the context of transport to a microtome, and the sectioning operation with the microtome, for example, can thus be carried out without difficulty. Softening of the embedded block can be avoided because the processing stations are embodied to cool the portable device when it is in an attached state, and thus to cool the sample. After detachment from the embedding station, cooling can thus be continued by the portable device, in particular using the energy present in internal energy reservoirs of the portable device. In addition, after attachment of the, for example, preferably modularly embodied portable device onto the microtome, cooling of the samples can occur, for example, utilizing energy for cooling that is transferred from the microtome to the portable device.

What was explained above by way of example with reference to one processing station embodied as an embedding station and one as a microtome is also analogously the case when processing stations of other types, for example trimming stations or fixing stations or dehydration stations or cleaning stations or infiltration stations, are used.

The processing station has the further advantage of being able to dispense with an additional transport basket, since transportation of multiple samples between two processing stations can occur by means of the portable device and thus not by means of a separate transport basket. No additional storage space is needed for the portable device, since it can be attached onto the processing station and thus stored there.

In addition, in the case of a processing station in the form of a trimming station that is embodied to cool the samples, it is possible to ensure that a sample breakdown process occurs only slowly. More time thus remains, as compared with the known embodiments in which no cooling of the sample occurs, for introducing the samples into a fixing agent. As a result, it is possible to ensure that the treatment process is accomplished with a high-quality sample.

In an advantageous embodiment, the processing station comprises an attachment interface with which the portable device is attachable to the processing station.

Coupling of the portable device onto the processing station can be accomplished via direct or indirect coupling. The portable device and the processing station can be in direct or indirect contact in the attached state.

Provision can be made in particular that the attachment interface comprises a counter-coupling element that is attachable to a coupling element of the portable device.

The counter-coupling element can be a mechanical and/or electrical coupling means. The mechanical coupling means can produce a positively engaged and/or frictionally engaged connection between the processing station and the portable device. The electrical coupling means can be connected to an energy supply unit, for example to a current source. Upon attachment of the portable device to the processing station, an electrical connection between the portable device and the processing station can be produced via the electrical coupling means.

A coupling element that is attachable, for example in positively engaged fashion, to a counter-coupling element offers the advantage that the user can be informed, for example by way of the external shape of the coupling element and counter-coupling element, as to how the portable device is to be attached to the processing station.

A further advantage is the fact that secure and mechanically stable attachment of the portable device to the processing station can be achieved by means of the coupling element. The coupling means and/or the counter-coupling element can in that regard be embodied in particular as mechanical coupling means. The mechanical coupling means can, for example, produce a positively engaged and/or frictionally engaged connection between the portable device and the processing station.

In a particular embodiment, the coupling means produces, with the portable device in the state attached to the processing station, an electrical connection between the portable device and the processing station. Provision can also be made in particular that electrical signals and/or electrical energy, for example electrical energy for cooling with an active cooling component such as Peltier element, is transferred via the coupling means and the counter-coupling element. The coupling means and/or the counter-coupling element can in that regard be embodied in particular as electrical coupling means.

Provision can also be made in particular that a mechanical and/or electrical plug connection can be produced with the coupling means and the counter-coupling element.

An attachment interface of a first processing station can be embodied identically to an attachment interface of a second processing station. Thanks to an identically embodied attachment interface in multiple processing stations, it is possible to ensure that the same portable device can be attached to multiple processing stations. The attachment interface can be defined by the configuration and the physical positioning of the counter-coupling element of the processing station.

In a particular embodiment, the portable device comprises a sensor unit. The sensor unit can ascertain whether or not the portable device is coupled to the processing station. For example, for the case in which the sensor ascertains that the portable device is not attached to the processing station, cooling of the sample utilizing, for example, the energy stored in the portable device, in particular by means of an active cooling device of the device for transportation, such as e.g. a Peltier element, can be effected. In this case the sensor unit can cause the electrical energy stored in the reservoir to be delivered to the Peltier element.

As already mentioned, provision can advantageously be made that the attachment interface comprises a receptacle for receiving the portable device. The receptacle can be, for example, an indentation in the housing of the processing station or a holder of the processing station, into which the portable device can be temporarily inserted entirely or in part. Provision of the receptacle makes it possible to ensure that attachment of the portable device to the processing station is possible in simple fashion. In particular, the user can detect without difficulty exactly where on the processing station the portable device is to be attached.

The portable device can be received in the receptacle upon attachment to the processing station. The receptacle can be a constituent of a cooling system of the processing station. The cooling system can be, for example, a closed cooling circuit that comprises, inter alia, a compressor.

In a particularly advantageous embodiment, provision is made that the processing station has an independent cooling system. The independent cooling system can also, for example, be embodied to cool regions of the processing station that have nothing directly to do with the portable device.

In an advantageous embodiment of a processing station according to the present invention, provision is made that the portable device is connectable to the cooling system of the processing station. In particular, provision can advantageously be made that the processing station comprises an independent cooling system that is automatically connected to a portable device as soon as the latter is attached to the processing station. For this, for example, immediately upon attachment supply lines that can be, for example, electrical leads or coolant lines are connected to one another, and at least one supply switch and/or at least one supply valve is automatically opened. Provision can be made here that the supply switch and/or supply valve is closed again automatically upon detachment of the portable device.

The cooling system provided in the processing station can be activated when the portable device is attached to the processing station, in particular to the receptacle of the processing station. This offers the advantage that cooling of the sample by the cooling system occurs only when it is actually required.

In a particular embodiment, provision is made that the attachment interface is arranged outside of, in particular adjacent to, a processing space of the processing stations. The attachment interface is preferably located outside the spaces in which the actual processing operation, for example cutting, infiltration, fixing, embedding, takes place using a processing apparatus. This ensures in particular that the processing apparatus can be used, for example, irrespective of the attachment interface, even when a portable device is not currently attached.

The processing station according to the present invention can be embodied, for example, as a trimming station or as a fixing station or as a dehydration station or as a cleaning station or as an infiltration station or as an embedding station or as a microtome.

A system having at least one portable device according to the present invention and having at least one processing station according to the present invention is particularly advantageous. A system having a portable device, by preference having a plurality of portable devices, and having multiple processing stations each one of which comprises an attachment interface for attachment of the portable device, is, however, very particularly advantageous. In such a system, the attachment interface of one processing station is preferably configured identically to the attachment interface of another processing station. This ensures that the portable devices, together with the samples placed thereon, can be transported back and forth as desired between the processing stations, and can be attached respectively to a processing station.

As already mentioned, provision can advantageously be made that the portable device, in particular the coupling element of the portable device, is embodied in such a way that the portable device, after detachment from the processing station, is attachable to another processing station or to the same processing station.

After detachment of the portable device, another portable device can be attached to the processing station, so that the processing operation of the respective processing station does not need to be interrupted.

The subject matter of the invention is schematically depicted in the drawings and will be described below with reference to the FIGURE; identical or identically functioning elements are provided in most cases with the same reference characters.

BRIEF DESCRIPTION OF THE DRAWING VIEW

DETAILED DESCRIPTION OF THE INVENTION

Figure 1:
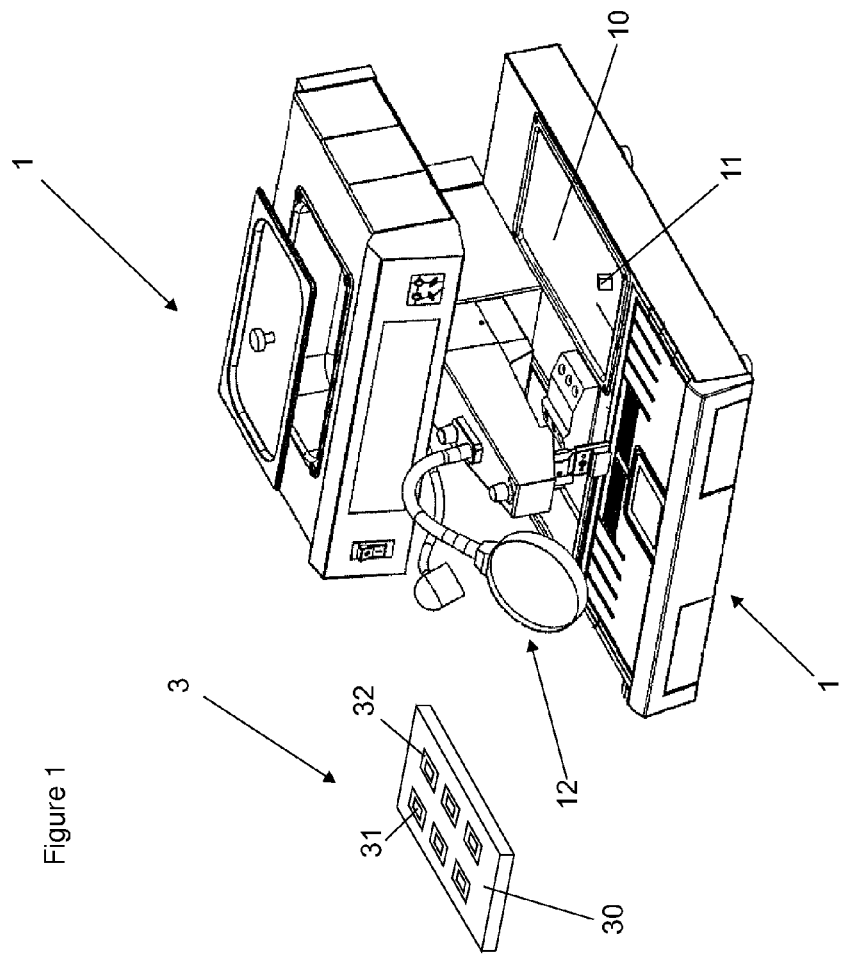
FIG. 1 is a perspective depiction of a system made up of an embedding station, a microtome, and a portable device.
Figure 1:
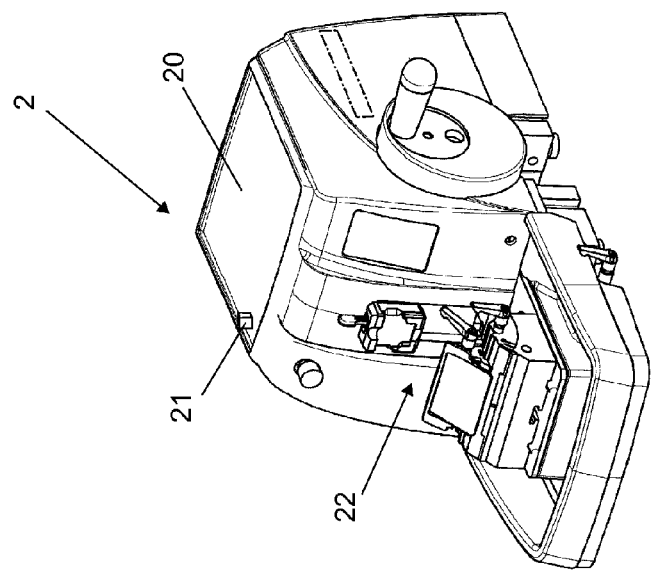
Figure 2:
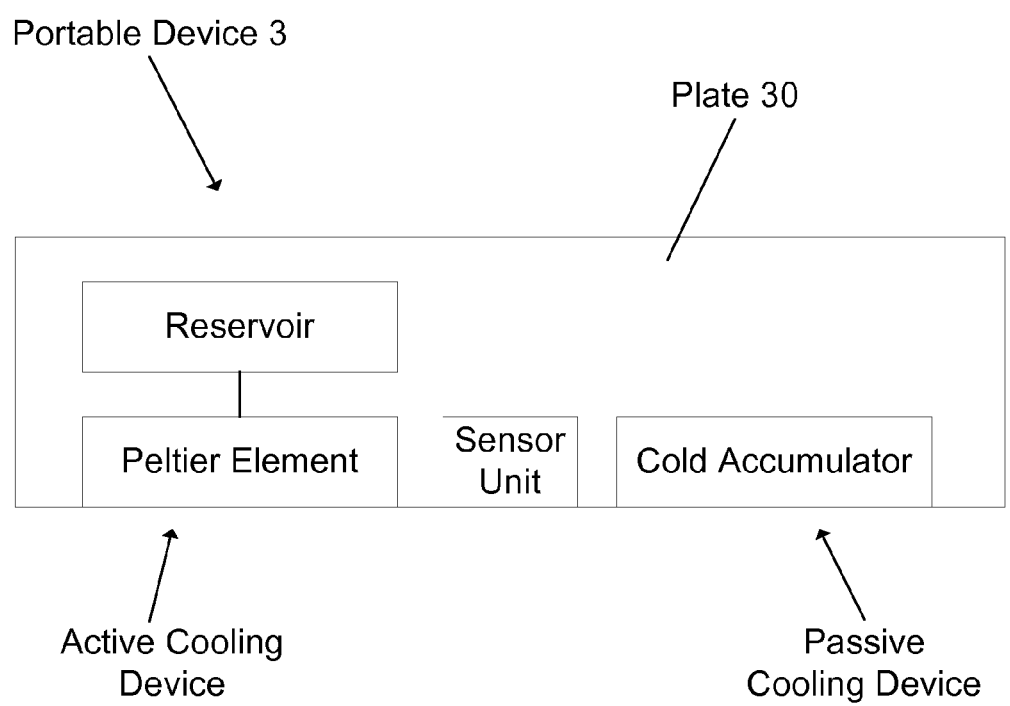
FIG. 2 is a cross-sectional block diagram of an embodiment of a portable device in accordance with the present disclosure.

The system depicted in FIG. 1 comprises an embedding station 1, a microtome 2, and a portable device 3. FIG. 1 depicts a state in which portable device 3 is not attached either to embedding station 1 or to microtome 2.

Embedding station 1 comprises a receptacle 10 for receiving portable device 3. The receptacle is a constituent of a cooling system (not depicted in detail) of embedding station 1. The cooling system of embedding station 1 is preferably deactivated as long as portable device 3 is not attached to embedding station 1. After attachment of portable device 3 to embedding station 1, the cooling system is activated, with the result that receptacle 10 and thus portable device 3 are cooled.

Extending from receptacle 10 is a counter-coupling element 11 that is connected to an energy supply unit (not depicted). Upon attachment of portable device 3 to embedding station 1, counter-coupling element 11 becomes coupled to a coupling element (not depicted) of portable device 3. Portable device 3 can be mechanically and electrically attached to embedding station 1 by means of counter-coupling element 11. In the attached state, portable device 3 is in direct contact with receptacle 10.

Receptacle 10 is arranged alongside and adjacent to a processing space of embedding station 1. Embedding of the histological samples occurs in the processing space by means of a variety of processing means 12 of embedding station 1.

Microtome 2 comprises a receptacle 20 for receiving portable device 3, which is arranged on an upper side of microtome 2. Extending from receptacle 20 is a counter-coupling element 21 that is connected to an energy supply unit (not depicted) of microtome 2. Counter-coupling element 21 of microtome 2 is embodied analogously to counter-coupling element 11 of embedding station 1.

Counter-coupling element 21 of microtome 2 is moreover positioned in receptacle 20 of microtome 2 in such a way that counter-coupling element 21 can be coupled to the coupling element of portable device 3. Counter-coupling element 11 of embedding station 1 is likewise positioned in receptacle 10 of embedding station 1 in such a way that counter-coupling element 11 can be coupled to the coupling element of portable device 3.

Portable device 3 can be mechanically and electrically attached to microtome 2 by means of counter-coupling element 21 of microtome 2. Microtome 2 depicted in FIG. 1 does not comprise a cooling system, so that no cooling of the samples present in portable device 3 can occur via receptacle 20. Also conceivable, of course, are microtomes 2 that comprise a cooling system, so that cooling of the samples present in portable device 3 can occur via receptacle 20.

Portable device 3 comprises a plate 30 that comprises a plurality of recesses 32. One cassette 31 is arranged in each of recesses 32. An embedded block (not depicted in the FIGURE) that contains at least one sample is mounted on the cassette. Portable device 3 comprises a coupling element (not depicted), for example in the form of a recess. Upon attachment of the portable device to embedding station 1 or to microtome 2, the coupling element of portable device 3 becomes coupled to counter-coupling element 11, 21 of embedding station 1 or of microtome 2. Plate 30 is dimensioned in such a way that portable device 3 can be placed onto receptacle 10, 20 of embedding station 1 or of microtome 2. Portable device 3 moreover comprises a cooling device, in particular an active cooling device such as a Peltier element.

The manner of operation of the system depicted in FIG. 1 will be explained below. Prior to embedding, the samples are introduced into a mold. Embedding medium is then delivered through an opening into the mold, and a cassette 31 is placed onto the mold in such a way that cassette 31 at least partly closes off the opening of the mold. The mold with the sample, and cassette 31, are introduced into recess 32 of portable device 3. The cooling system of embedding station 1 is activated, since portable device 3 is attached to embedding station 1, so that cooling of the sample occurs. In particular, the cooling system produces a heat flux from the sample via plate 30 and receptacle 10 into a coolant of the cooling system, with the result that cooling of the samples occurs. Alternatively or additionally, cooling can also occur by way of a cooling device of portable device 3.

After hardening of the histological samples, the embedding agent has solidified into an embedded block and the sample is immobilized in stationary fashion therein. The embedded block is joined to the cassette. The mold can be separated from the embedded block, the sample, and the cassette at the embedding station, or only after transport to microtome 2. Portable device 3 is detached from embedding station 1, and transported to microtome 2 and attached thereto.

During transport, the sample continues to be cooled via a cooling device of portable device 3, for example a Peltier element, that obtains energy from an electrical rechargeable battery of the portable device.

Portable device 3 is set onto receptacle 20 of microtome 2 in such a way that the coupling element (not depicted) of the portable device is coupled to counter-coupling element 21.

The samples and cassettes 31 present in recesses 32 continue to be cooled after the attachment of portable device 3 to microtome 2, so that the embedded block does not soften. This is possible because microtome 2 supplies electrical energy via counter-coupling element 21 to the cooling device, in particular active cooling device, provided in portable device 3. Cooling of the samples can occur as a result of the provision of electrical energy to the cooling device, in particular the Peltier element, of portable device 3.

The laboratory worker can remove cassettes 31, with the embedded block fastened thereto, from portable device 3 and process them using processing means 22 of microtome 2.

PARTS LIST

1 Embedding station
2 Microtome
3 Portable device
10 Receptacle of embedding station
11 Counter-coupling element of embedding station
12 Processing means of embedding station
20 Receptacle of microtome
21 Counter-coupling element of microtome
22 Sectioning means
30 Plate
31 Cassette
32 Recess

What is claimed is:

1. A portable device (3) for transporting at least one histological sample or at least one cassette (31) containing a histological sample, wherein the device (3) is attachable to a processing station for processing histological samples, wherein the device (3) is embodied to continuously cool the sample to be carried during the transporting, wherein, in an attached state, energy for cooling is transferrable between the processing station and the device (3), wherein the device (3) includes an active cooling device and a reservoir for electrical energy, and wherein the reservoir is connected to the active cooling device;
wherein the device (3) has at least one coupling element that is coupled to a counter-coupling element (11, 21) of the processing station in an attached state such that energy is supplied by the processing station to the reservoir of the device (3) in the attached state; and
wherein the reservoir is configured to provide energy to the active cooling device to enable the active cooling device to continuously cool the sample when the device (3) is detached from the processing station for transport.

2. The portable device (3) according to claim 1, wherein energy for cooling is transferrable from the processing station to the device (3).

3. The portable device (3) according to claim 1, wherein energy for cooling is transferrable from the device (3) to the processing station.

4. The portable device (3) according to claim 1, wherein the coupling element is a mechanical coupling means, an electrical coupling means, or an electro-mechanical coupling means.

5. The portable device (3) according to claim 1, wherein the active cooling device comprises a Peltier element.

6. The portable device (3) according to claim 1, wherein the portable device (3) includes a passive cooling device.

7. The portable device (3) according to claim 6, wherein the passive cooling device comprises a cold accumulator.

8. The portable device (3) according to claim 1, wherein at least some of the energy for cooling is transferrable in the form of electrical energy.

9. The portable device (3) according to claim 1, wherein at least some of the energy for cooling is transferrable in the form of a heat flux.

10. The portable device (3) according to claim 1, wherein at least some of the energy for cooling is transferrable by conveying a coolant.

11. The portable device (3) according to claim 1, wherein the portable device (3) includes at least one recess (32) configured for reception of a sample or cassette (31).

12. The portable device (3) according to claim 1, wherein the portable device (3) includes a sensor unit for ascertaining whether the portable device (3) is attached to a processing station.

13. The portable device (3) according to claim 1, wherein the portable device (3) is attachable, after detachment from the processing station, to another processing station or again to the same processing station.

14. A processing station for processing a histological sample, wherein the processing station is embodied for releasable attachment of a portable device (3) for transporting at least one histological sample or at least one cassette (31) containing a histological sample, and is embodied to transfer energy for cooling to, or receive energy for cooling from, an attached portable device (3), wherein the processing station comprises an independent cooling system, wherein the processing station comprises an attachment interface with which the portable device (3) is attachable to the processing station, wherein the attachment interface comprises a counter-coupling element (21) attachable to a coupling element of the portable device (3), wherein the counter-coupling element (21) is an electrical counter-coupling element or an electro-mechanical counter-coupling element, wherein the portable device (3) has an active cooling device and a reservoir for electrical energy, and wherein the processing station is configured to supply energy to the reservoir when the portable device (3) is attached to the processing station.

15. The processing station according to claim 14, wherein the attachment interface comprises a receptacle (10, 20) for receiving the portable device (3).

16. The processing station according to claim 15, wherein the attachment interface is arranged outside and adjacent to a processing space of the processing station.

17. The processing station according to claim 14, wherein the independent cooling system is connectable to an attached portable device (3).

18. The processing station according to claim 17, wherein the independent cooling system is connected automatically to a portable device (3) as soon as the portable device is attached to the processing station.

19. The processing station according to claim 14, wherein the processing station is selected from a group of processing stations consisting of: a trimming station, a fixing station, a dehydration station, a cleaning station, an infiltration station, an embedding station (1), and a microtome (2).

20. A system comprising:
at least one portable device (3) configured for transporting at least one histological sample or at least one cassette (31) containing a histological sample; and
a processing station for processing a histological sample, wherein the portable device (3) is attachable to the processing station;
wherein the portable device (3) is embodied to continuously cool the sample to be carried during the transporting, wherein energy for cooling is transferred between the processing station and the portable device (3) when the portable device is attached to the processing station, wherein the device (3) includes an active cooling device and a reservoir for electrical energy, wherein the reservoir is connected to the active cooling device, wherein the device (3) has at least one coupling element that is coupled to a counter-coupling element (11, 21) of the processing station in an attached state such that energy is supplied by the processing station to the reservoir of the device (3) in the attached state, and wherein the reservoir is configured to provide energy to the active cooling device to enable the active cooling device to continuously cool the sample when the device (3) is detached from the processing station for transport.

21. The system according to claim 20, wherein the system comprises a plurality of processing stations, each processing station including an attachment interface for attachment of the at least one portable device (3).

22. The system according to claim 21, wherein the attachment interface of one processing station is identical to the attachment interface of another processing station.

* * * * *